United States Patent [19]

Kramer

[11] Patent Number: 5,297,714
[45] Date of Patent: Mar. 29, 1994

[54] SURGICAL STAPLE WITH MODIFIED "B" SHAPED CONFIGURATION

[75] Inventor: Frank Kramer, Edgewood, Ky.
[73] Assignee: Ethicon, Inc., Somerville, N.J.
[21] Appl. No.: 686,646
[22] Filed: Apr. 17, 1991
[51] Int. Cl.$^5$ ............................................. A61B 17/00
[52] U.S. Cl. ..................................... 227/175; 606/219; 227/62
[58] Field of Search ................... 606/219; 227/61, 62, 227/901, 902, 175

[56] References Cited

U.S. PATENT DOCUMENTS

| | | | |
|---|---|---|---|
| 4,014,492 | 3/1977 | Rothfuss | 606/219 X |
| 4,467,805 | 8/1984 | Fukuda | 606/219 |
| 4,610,251 | 9/1986 | Kumar | 606/219 |
| 4,762,260 | 8/1988 | Richards et al. | 227/19 |
| 4,887,601 | 12/1989 | Richards | 606/219 |

Primary Examiner—Stephen C. Pellegrino
Assistant Examiner—Jeffrey A. Schmidt
Attorney, Agent, or Firm—Paul A. Coletti

[57] ABSTRACT

A surgical staple is used in joining the skin or fascia of a patient, and is especially desired to be used with mesh placed over a cut organ, such as the kidney. The staple is adapted to be formed about a central anvil and former. The configuration of the staple is such that at initial contact the points of the staple are formed at acute angles to the central portion of the staple. In this fashion, upon forming, a modified "B" shape is derived. This configuration has proven useful to reduce rotation of the staple when emplaced over mesh.

6 Claims, 3 Drawing Sheets

SURGICAL STAPLE WITH MODIFIED "B" SHAPED CONFIGURATION

BACKGROUND OF THE INVENTION

Surgeons have come to use staples for closing wounds or incisions in the skin and fascia instead of conventional thread sutures in surgical operations. One of the main reasons for this trend is that the conventional suture which involves insertion of a thread means by a curved needle and then tying the ends of the thread is quite time-consuming. There are various operations in which a large number of sutures must be used. Thus, for example, in heart surgery where coronary by-pass procedures are performed, the by-passes are usually made from the saphenous vein in the leg. It is common to perform as many as six incisions in the leg from the ankle to the groin in dissecting out the saphenous vein from which the by-passes are to be made. The several incisions involved may vary from perhaps two inches in length to six or seven inches in length. With conventional thread sutures the closing of such wounds would take perhaps an hour to an hour and a half, whereas with surgical staples as many as fifty staples may be emplaced in a matter of ten to twenty minutes. This saving of time is of great importance in that it not only saves the surgeon's time but it reduces fatigue on the part of the surgeon and it substantially reduces the length of time the patient must be maintained under anesthesia. It is generally recognized that the shorter the time the patient is under anesthesia, the more rapid is his recovery and the less trauma is involved.

Some presently available surgical staples are generally shaped like conventional staples that are used in wood or paper except that they are generally wider and have short legs. They are formed about an anvil into a box configuration. There has been observed a tendency for the points of such staples to slide across the skin along their cut surfaces before penetrating and in doing so the staples may tend to separate the wound before the points actually penetrate the skin. In the conventional staple, the points are relatively close to the forming corners of the anvil about which they are formed when the staple first contacts the skin and again when the staple contacts the anvil. Thus, they do not always obtain a secure and effective wound closing since in order to accomplish this the staple must gather skin and tissue sufficiently to close the wound and to cause the edges of the wound to be brought into approximation.

The staple according to Rothfuss, U.S. Pat. No. 4,014,492 prior to emplacement is configured with a central portion, a straight portion extending upwardly and outwardly from each end of the central portion at an obtuse angle, and a relatively short straight portion extending downwardly and outwardly from each of said upwardly and outwardly extending portions. The downwardly and outwardly extending portions have vertical cuts to produce sharp points at the ends of the downwardly and outwardly extending portions. The vertical cuts will be normal to the surface of the skin at the time of initial contact. The disposition of the points with respect to the forming anvil produces an eversion of the wound which insures proper approximation and better and more rapid healing.

In Becht, et al., U.S. Pat. No. 4,261,244, there is provided in a surgical staple for use in suturing the skin or fascia of a patient and of the type having an elongated, substantially horizontal crown portion terminating in downwardly depending leg portions having points formed at their free ends, the surgical staple, together with a plurality of identical surgical staples, being adapted to straddle and to be fed along guide means to the anvil of a surgical stapling instrument which bends end portions of the surgical staple crown downwardly so that the leg portions are substantially coaxial with their points approaching each other.

The improvement in Becht '244 comprises a first pair of diametrically opposed front and rear flats and a second pair of diametrically opposed top and bottom flats on the surgical staple. The front and rear flats of the first pair extend respectively along the front and rear of the crown and leg portions of the surgical staple. The diametrically opposed flats of the second pair are disposed at 90° to the first pair of flats. The top flat of the second pair extends along the upper surface of the surgical staple crown portion and the outsides of its leg portions and the bottom flat of the second pair extends along the underside of the surgical staple crown portion and along the insides of its leg portions. The front and rear flats of the first pair, cooperate with similar flats on adjacent surgical staples, to assure proper feeding of the surgical staple along the surgical instrument guide means. The top and bottom flats of the second pair, cooperate respectively with the surgical stapling instrument former and anvil, to prevent undesirable axial rotation of the surgical staple crown portion during the forming and implanting thereof in the skin or fascia of a patient.

Staples of the referenced art and of the present invention are provided in a cartridge, and the configuration of the staple disclosed herein substantially improves the space factor and makes it possible to stack more staples in a given space in a cartridge than is possible with staples of conventional form.

Yet, certain deficiencies have been noted in current surgical staples. If the user wishes to staple mesh around, for instance, a blood vessel, or there is an organ needed to hold closed by mesh, it is difficult to staple current shaped staples into this mesh. That is, the staples hold the mesh materials loosely, and in some instances too loosely. It would be more desirable to have a staple which holds mesh more snugly, and yet remains easy to form. Also, of course, it would be desirable that this staple is capable of emplacement, either in tissue or in mesh, without rotation. The staples of this sort are more conducive, to withstand rotation also, if they are not "box" shaped. At times, the box shaped staples are difficult to form so that the entire box is closed, and appropriate tissue eversion is derived. Therefore, at times it may be more preferential to form a surgical staple in a non-box shaped configuration.

SUMMARY OF THE INVENTION

Therefore, it is an object of the invention to provide a staple capable of being formed in mesh, in conjunction with an anvil.

It is further an object of the invention to form a surgical staple containing a shape such that it is conducive to appropriate tissue eversion, if that is so desired.

It is yet another object of the invention to form a surgical staple such that rotation is not capable after the staple is formed.

Finally, it is another object of the invention to form a staple in a non-box shaped configuration so that the appropriate closure and tissue eversion of the staple is created.

These and other objects of the invention are provided in a surgical staple having a crown length and containing legs which are formed at acute angles to the crown. The legs may be formed at angles of up to 60° with the crown. The crown itself may be in a standard straight form or a "gull wing" form, much as is disclosed in the previously cited references. When formed, the staple is wrapped around a central anvil and shaped by a forming mechanism such that the angularly displaced legs are shaped such that the final version is much like an indented rectangle, or a modified "B" shape. This shape is capable of producing the desired effects, and is useful in situations where conventional staples shapes were heretofore less desirable.

The invention will be better understood with reference to the attached drawings and detailed description of the invention.

DETAILED DESCRIPTION OF THE INVENTION

Figure 1:
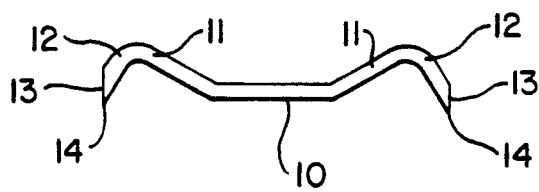
FIG. 1 is an elevational view of a prior art surgical staple.

As seen in FIG. 1 the prior art staple has a central portion 10 with upwardly and outwardly extending portions 11 which extend at an obtuse angle to the portion 10. From the ends of the portions 11 there extend downwardly and outwardly the portions 12 which are shown as disposed at substantially right angles to the portions 11. The ends of the portions 12 are cut vertically as at 13 to provide the sharp points 14.

In FIGS. 3, 4, 5 and 6 inclusive, the emplacement of a staple to close the wound is shown progressively. In these Figures, the forming anvil about which the staple is formed is indicated at 15 and the driver or forming die of a surgical stapler is indicated at 16. The skin of the patient is indicated at 17 and the underlying tissues at 18. The incision which is being closed is indicated at 19.

Figure 3:
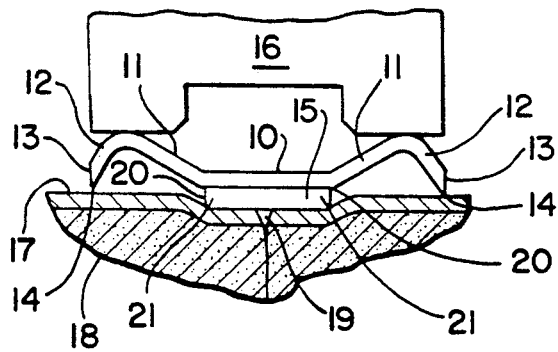
FIG. 3 is an elevational view showing the prior art staple in relation to a forming anvil, a forming die, and a wound which is to be closed.

FIGS. 3 serves to illustrate the disposition of the points 14 with respect to the anvil 15. It will be noted that the upper corners of the anvil are curved as indicated at 20 and the radii of curvature of the curves 20 are indicated by the points 21. It will be observed that the points 14 of the staple are approximately in the plane of the centers of curvature 21 of the curves 20. This configuration insures that the first bending effort of the die 16 against the portions 11 produces a penetration of the skin by the points 14 rather than a sliding of the points along the skin and insures greater skin gathering than hitherto obtained.

Figure 4:
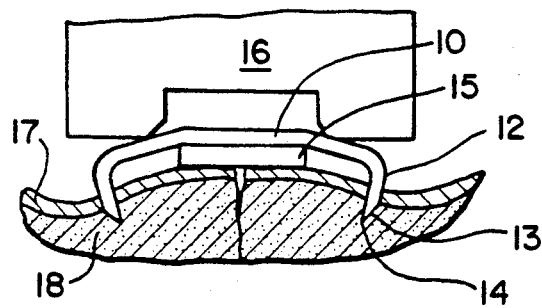

In FIG. 4 the points 14 have penetrated the skin 17 and underlying tissues 18 and it will be seen that the portions 11 and 12 of the staple are being bent in a curve about the points 21.

Figure 5:
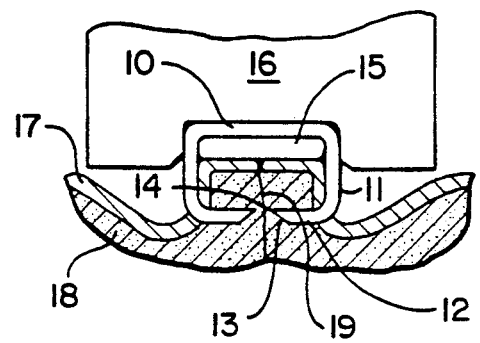
FIGS. 4, 5 and 6 are views similar to the views of FIG. 3 showing the staples in the process of being formed; and after the stapler and anvil have been removed.
Figure 2:
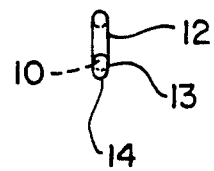
FIG. 2 is an elevational view of the staple of FIG. 1.
Figure 6:
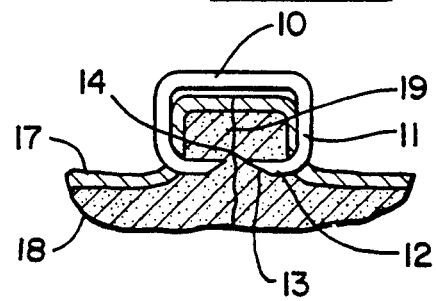

In FIG. 5 the staple has been completely formed and in FIG. 6 the tool and anvil have been withdrawn, i.e. the formed staple has been ejected from the tool and anvil. It will be seen that the incision is nicely closed and is properly everted to produce the desired approximation and to enhance the healing process.

Figure 7A:
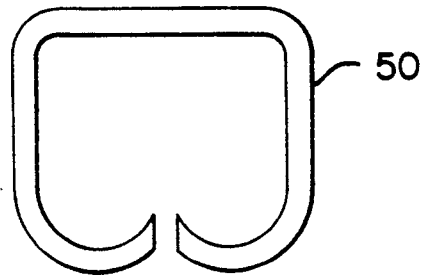
FIG. 7A shows an alternative embodiment of a prior art staple.

Alternately, in other staples like staple 50 in FIG. 7A, the final shape is formed in a curve, so that the box shape is refined. This staple uses an anvil 60 for forming, such as those found in internal surgical stapling devices.

Figure 1A:
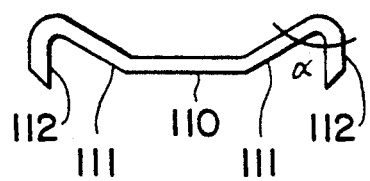
FIG. 1A is an elevational view of a first preferred embodiment of a surgical staples according to the invention.
Figure 1B:
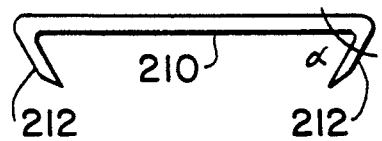
FIG. 1B is an elevational view of a second preferred embodiment of a surgical staples according to the invention.

Now, as seen in FIGS. 1A and 1B, the staple of this invention has a central portion 110, 210. In FIG. 1A, this central portion 110 has upwardly and outwardly extending portions 111, which extend at an obtuse angle to the portion 110. The staple as in FIG. 1B does not contain such an upwardly and outwardly extending portion. From the end of the portions 111, or the central portion 210 in FIG. 1B, there extends downwardly the portions 112, 212. These leg portions form the essential aspects of this invention. The leg portions, 112, 212 are disposed at substantially acute angles to the portions 111, 210. This acute angle is indicated as angle α and differs from the essentially right angle formed between portions 111 and 112 as seen in FIG. 1. The ends of the portions 112, 212 are cut vertically as at 113, 213 to provide sharp points 114, 214.

Figure 2A:
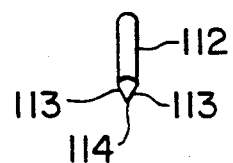
FIG. 2A is an elevational view of the staple of FIG. 1A.
Figure 2B:
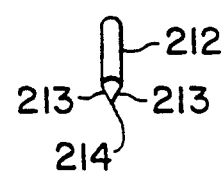
FIG. 2B is an elevational end view of the staple of FIG. 1B.

As seen in FIGS. 2A and 2B these staples are formed with very similar end views as with the staple shown in FIG. 1.

As seen in FIGS. 3A, 4A, 5A, 6A and FIGS. 3B, 4B, 5B and 6B inclusive, the placement of the staple of this invention to close a wound or be closed over mesh is shown progressively.

As seen in each of these Figures, there is includes a mesh covering such as may be found over those mesh coverings used in treatment of kidney closure or other organ closures. This mesh is labeled in each of the Figures as M. In these Figures, the forming anvil about which the staple is formed is the same anvil 15 and the forming die is the same die 16 as indicated in the set of FIGS. 3-5. The skin of the patient is again indicated at 17 and the underlying tissues at 18. The incision which is to be closed is indicated at 19.

Figure 3A:
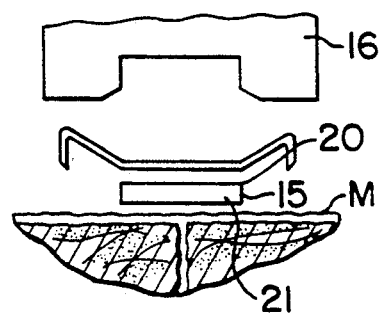
FIG. 3A is an elevational end view of the staple of FIG. 1A showing the present invention in relation to a forming die, a forming anvil, and a wound which is to be closed.
Figure 3B:
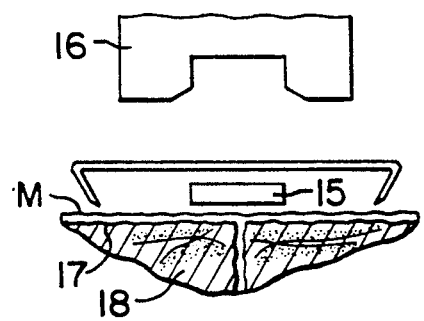
FIG. 3B is an elevational view of the second preferred embodiment of the present invention in relation to a forming anvil, a forming die, and a wound which is to be closed.

FIGS. 3A and 3B serve to illustrate that this position of the points 114, 214 with respect to anvil 15. It will be noted that the upper corners of the anvil are curved so as to again curve the staples 100, 200. The points 114, 214 of each of these staples are approximately in the plane, or above, the centers of curvature 21 of each of the curves 20. The configuration as created in the staples of this invention insures that the first bending effort of the die 16 against the portions 110, 210 produces an inverted penetration of the skin by the points 114, 214, or even a desired missing of the skin and enclosure over mesh. Again, however, there is no sliding of points along the skin so that, if desired, greater skin gathering is still obtained.

Figure 4A:
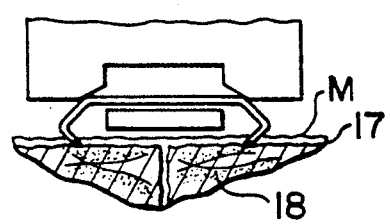
FIGS. 4A, 5A and 6A are views showing the present invention in which the staple is formed and after the stapler and anvil have been removed.
Figure 4B:
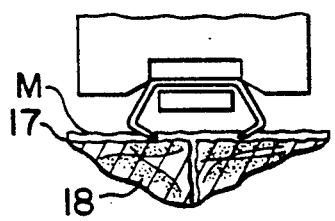
FIGS. 4B, 5B and 6B are views showing the second preferred embodiment of the staple of the invention being formed, and after the stapler and anvil have been removed.

In FIGS. 4A and 4B, it will be noticed that the penetration of the staples is now identical and that the points 114, 214 have penetrated the skin and mesh and the underlying tissues 18 and it will be seen that the portion 110, 210 of the staples 100, 200 are bent in a curve around the points 21.

Figure 5A:
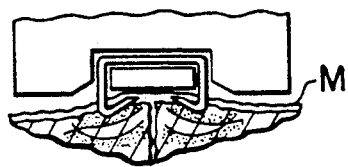
Figure 5B:
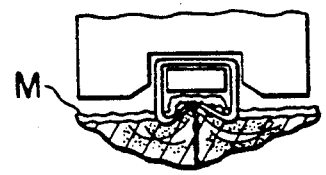
Figure 6A:
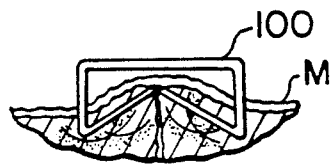
Figure 6B:
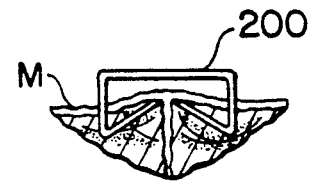

In FIGS. 5A and 5B, the staple has been completely formed and in FIGS. 6A, 6B, the tool and anvil have been withdrawn. Now, the formed staples 100, 200 are ejected from the stapler and it is seen that the incision is nicely closed and yet gathered in an upward B position. Or, as in FIG. 6B, the user has closed the staple such that the tissue has not been gathered and only the mesh is gathered. This may also be done over areas were it is desired only to gather mesh and not to close wounds.

Figure 7:
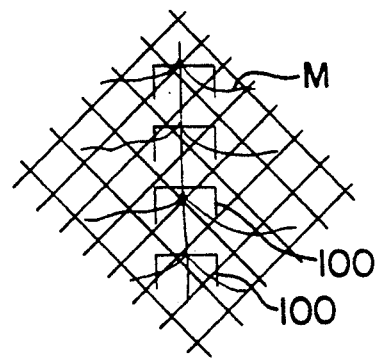
FIG. 7 shows a series of formed staples such as those described in FIGS. 6A and 6B, as emplaced in tissue.

In this way, each of the staples 100, 200 as seen in FIGS. 6A, 6B have now been properly closed and formed a modified "B" shape. In this way, also, each of the staples has gathered only the appropriate amounts of tissue and is not shaped in a box. This reduces the possibility of rotation of the staples during staple forming, essentially by creating an additional dimension in the place of the staple, so that an additional degree of freedom in the staple is defeated. As seen in FIG. 7, the closed wound with the wound properly everted and the modified B shaped staple with mesh contained therein is shown.

It is to be noted, that the angle α as between the formed legs in this staple should be no more than 75° and preferably less than 60°. It has been found that enclosed angles of up to 45° may be desirable, in cases where rotation of the staple is expressly desired to be limited, such as in the use of very loose meshes.

Again, as in the referenced art, the staples are easy to stack and take up only as much space as the prior art staples. They are also easy to drive into tissue, and like the prior art, may be formed in square, rectangular or circular cross-sections. It is therefore to be understood that the embodiments of the invention are to be derived from the following claims and their equivalents.

What is claimed:
1. In combination:
   a surgical stapler having an anvil, and a driver for forming staples about said anvil, and
   a plurality of staples contained in said stapler, each said staple having:
   a preformed configuration with a straight crown having a driver facing side and an anvil facing side, and said crown having two ends; a pair of intermediate straight portions, each said intermediate straight portion extending from an end of said crown, and each said intermediate portion forming an obtuse angle with said crown on the driver facing side of said staple; and a pair of straight leg portions, each said leg portion with two ends and attached to an intermediate portion at one of said leg portion ends, said intermediate portions and said leg portions forming an acute angle toward said anvil facing side of said crown; and said leg portions having a sharpened tip at the second of said ends;
   said staples engageable with said anvil and said driver, such that said river is capable of causing a said staple to end about said anvil; and
   wherein a staple formed by said driver has a B shape, with said B shape having only straight segments.
2. The staple of claim 1 wherein said acute angles are between about 30° and 75°.
3. The combination of claim 1 wherein said crown is approximately the length of said anvil.
4. A method for forming staples comprising:
   providing a surgical stapler having an anvil, and a driver for forming staples about said anvil; and
   a plurality of staples, each said staple having:
   a preformed configuration with a straight crown having a driver facing side and an anvil facing side, and said crown having two ends; a pair of intermediate straight portions, each said intermediate straight portion extending from an end of said crown, and each said intermediate portion forming an obtuse angle with said crown on the driver facing side of said staple; and a pair of straight leg portions, each said leg portion with two ends and attached to an intermediate portion at one of said leg portion ends, said intermediate portions and said leg portions forming an acute angle toward said anvil facing side of said crown; and said leg portions having a sharpened tip at the second of said ends;
   said staples engageable with said anvil and said driver, such that said river is capable of causing a said staple to bend about said anvil;
   moving said river toward said anvil with a said staple crown placed on said anvil; and
   using said driver to bend said staple about said anvil, wherein a staple formed by said driver has a B shape, with said B shape having only straight segments.
5. The method of claim 4 wherein said acute angles are between about 30° and 75°.
6. The method of claim 4 wherein said crown is approximately the length of said anvil.

* * * * *